(12) United States Patent
Cassels et al.

(10) Patent No.: US 7,217,541 B2
(45) Date of Patent: May 15, 2007

(54) **METHOD OF MAKING CS6 ANTIGEN VACCINE FOR TREATING, PREVENTING, OR INHIBITING ENTEROTOXIGENIC *ESCHERICHIA COLI* INFECTIONS**

(75) Inventors: Frederick J. Cassels, Ellicott City, MD (US); James F. Wood, Germantown, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 665 days.

(21) Appl. No.: 10/370,522

(22) Filed: Feb. 24, 2003

(65) Prior Publication Data

US 2004/0005662 A1 Jan. 8, 2004

Related U.S. Application Data

(60) Provisional application No. 60/361,105, filed on Feb. 25, 2002, provisional application No. 60/421,804, filed on Oct. 29, 2002.

(51) Int. Cl.
*A12P 21/04* (2006.01)
*C12N 15/09* (2006.01)
*C12N 1/20* (2006.01)
*C12P 21/06* (2006.01)

(52) U.S. Cl. .................. 435/71.1; 435/69.3; 435/69.1; 435/252.22; 435/848

(58) Field of Classification Search ............... 435/71.1, 435/69.3, 69.1, 252.33, 848; 424/242.1; 530/350, 825
See application file for complete search history.

(56) References Cited

U.S. PATENT DOCUMENTS

| | | | |
|---|---|---|---|
| 5,648,081 A * | 7/1997 | van den Bosch | 424/255.1 |
| 5,698,416 A | 12/1997 | Wolf et al. | 435/69.1 |
| 5,830,479 A * | 11/1998 | Emery et al. | 424/255.1 |
| 5,914,114 A | 6/1999 | Cassels | 424/241.1 |
| 5,935,838 A | 8/1999 | Askelöf et al. | 435/252.1 |
| 6,309,669 B1 | 10/2001 | Setterstrom et al. | 424/486 |
| 6,902,736 B2 * | 6/2005 | Altboum et al. | 424/242.1 |
| 2004/0156829 A1 * | 8/2004 | Wolf et al. | 424/93.2 |

FOREIGN PATENT DOCUMENTS

WO WO 02/064162 8/2002

OTHER PUBLICATIONS

Helander et al. J. Clin. Microbiol. 35: 867-872, 1997.*
Jones et al. J. Bacteriol. 146: 841-846, 1981.*
Cassels et al. Toxicon 36 (9): pp. 1231, Sep. 1998.*
Wolf (1997) "Occurrence, Distribution, and Associations of O and H Serogroups, Colonization Factor Antigens, and Toxins of Enterotoxigenic *Escherichia coli*", Clinical Microbiology Reviews, 10(4):569-584.
Cassels, et al. (1998) "Production and microencapsulation of enterotoxigenic *Escherichia coli* colonization factors in human use vaccines" Abstracts of the General Meeting of the Am. Society for Microbiology, Atlanta, GA, Abstract E-92.
Katz, et al. (2001) "Clinical evaluation of microencapsulated CS6 vaccine for enterotoxigenic *Escherichia coli* (ETEC) diarrhea in healthy adults" Vaccines for Enteric Diseases Ved, 7-9.
Katz, et al. (2003) "Oral immunization of adult volunteers with microencapsulated enterotoxigenic *Escherichia coli* (ETEC) CS6 antigen" Vaccine, Buterworth Scientific, Guilford, GB, 21(5-6):341-346.
Supplementary Partial EP Search Report mailed from EPO May 6, 2005.

* cited by examiner

*Primary Examiner*—S. Devi
(74) *Attorney, Agent, or Firm*—Elizabeth Arwine

(57) ABSTRACT

Disclosed herein are methods for making large amounts of highly pure colonization factors. The methods of the present invention differ from prior art methods in that host cells which express the colonization factor of interest are cultured in media comprising more than about 50 μg/l of an antibiotic, the media is centrifuged and then filtered with a 0.2 μm filter tangential flow cartridge and a 300,000 MW cut-off filter, and a divalent cation is added. As disclosed herein the colonization factors made by the method of the present invention may be used in pharmaceutical compositions and methods for treating or preventing enterotoxigenic *Escherichia coli* infections.

21 Claims, 5 Drawing Sheets

METHOD OF MAKING CS6 ANTIGEN VACCINE FOR TREATING, PREVENTING, OR INHIBITING ENTEROTOXIGENIC *ESCHERICHIA COLI* INFECTIONS

CROSS REFERENCE TO RELATED APPLICATIONS

This application claims the benefit of U.S. Provisional Patent Application Ser. Nos. 60/361,105, filed 25 Feb. 2002, and 60/421,804, filed 29 Oct. 2002, which are herein incorporated by reference in their entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention generally relates to the preparation of proteins. In particular, the present invention relates to the preparation and purification of large quantities of at least one colonization factor (CF) and methods of using thereof.

2. Description of the Related Art

Diarrhea caused by enterotoxigenic *Escherichia coli* (ETEC), commonly referred to as travelers' diarrhea, is a common health problem among travelers visiting less developed or tropical countries. See Peltola, H., et al. (1991) Lancet 338:1285–1289 and Ericsson, C. D. et al. (1993) Clin. Infect. Dis. 16:616–626. Diarrhea caused by ETEC and other ETEC infections are important concerns for military personnel when deployed to less developed countries. See Wolf, M. K., et al. (1993) Clin. Microbiol. 31:851–856 and Bourgeois, A. L., et al. (1993) Am. J. Trop. Med. Hyg. 48:243–248. ETEC may be transmitted by food or water contaminated with animal or human feces. ETEC produces two toxins, a heat-stable toxin (ST) and a heat-labile toxin (LT). ETEC infections may cause profuse watery diarrhea, abdominal cramping, fever, nausea, vomiting, chills, loss of appetite, headache, muscle aches, and bloating.

The current therapy for travelers' diarrhea is to initiate treatment with agents such as bismuth subsalicylate (Pepto-Bismol®), antidiarrheals such as diphenoxylate with atropine (Lomotil®), loperamide HCl (Immodium®), attapulgite (Kaopectate®) and the like, rehydration therapy, and combinations thereof. The majority of the treatments involve the non-specific removal of the offending agents (i.e. toxins) from the intestinal tract. Only in moderate to severe cases of diarrhea where distressing or incapacitating symptoms are reported is antimicrobial therapy recommended. ETEC is frequently resistant to common antibiotics such as trimethoprim-sulfamethoxazole and ampicillin. Fluoroquinolones such as ciprofloxacin have shown some efficacy. Antibiotics are not usually effective at reducing clinical symptoms of the disease and problems associated with antibiotic resistance can occur. Prophylactic use of antibiotics is not recommended. Thus, therapies that specifically remove ETEC from the intestine are needed to provide more effective treatments for ETEC diarrhea.

In order to initiate the infectious process of diarrhea, ETEC must adhere to the host intestinal epithelial cells via the binding between bacterial adhesions, colonization factors (CFs) and host receptors. This binding is commonly referred to as adhesion-receptor interaction. See Beachey, E. H. (1981) J. Infect. Dis. 143:325–345; Satterwhite, T. K., et al. (1978) Lancet 2:181–184; and Warner, L. and Y. S. Kim. (1989) "Intestinal Receptors for Microbial Attachment", Eds. M. J. G. Farthing, and G. T. Kensch, ENTERIC INFECTION: MECHANISMS, MANIFESTATIONS AND MANAGEMENT, pp. 31–40. Raven Press, New York. ETEC then causes secretory diarrhea by expressing toxins, heat-labile enterotoxin (LT) and heat-stabile enterotoxin (ST). CFs interact with receptors on the host epithelial cells allowing for adherence of the ETEC to the mucosa. See Cassels, F. J. and Wolf, M. W. (1995) J. Indust. Microbiol 15:214–2263. CFs include colonization factor antigens (CFAs), *coli* surface (CS), and putative colonization factors (PCFs). The CFs that are most commonly expressed by ETEC and therefore targeted as potential vaccine components include CFA/I, CS3 and CS6. See Wolf, M. K. (1997) Clin. Microbiol. Rev. 10(4):569–584; Tacket, C. O., et al. (1994) Vaccine 12(14): 1270–1274; Güereña-Burgueño, F., et al. (2002) Infect. Immun. 70(4):1874–1880; Jertborn, M., et al. (2001) Clin. and Diag. Laboratory Immun. 8(2): 424–428; Freedman, D. J., et al. (1998) J. Infect. Dis. 177(3):662–667; and Evans, D. G., et al. (1988) FEMS Micro. Immuno. 117–126. In both natural and in recombinant organisms, the production of CFA/I, CS3, and CS6 is under the control of temperature-regulated promoters.

Unfortunately, prior art methods for large-scale production of such colonization factors (CFs) have been unsatisfactory. In particular, prior art methods resulted in low yields of bacteria and the desired CF under great risks of contamination. For example, U.S. Pat. No. 5,698,416 discloses a process for fermenting and isolating CF based on an example at small scale. However, the levels of purity (70%) obtained by prior art processes were insufficient for approval by the U.S. Food and Drug Administration (FDA) for use in some human vaccine applications. In addition, the yields obtained by prior art processes were not amenable for conducting an FDA approved clinical trial.

Therefore, a need still exists for compositions for treating, preventing, or inhibiting ETEC infections, diseases, or disorders. In particular, a need exists for the preparation and purification of at least one CF in high purities and large amounts that are suitable for approval from governmental regulatory agencies for administration to humans.

SUMMARY OF THE INVENTION

The present invention generally relates to methods for producing large quantities of high purity, low endotoxin-containing colonization factors (CFs).

In some embodiments, the present invention provides a method of making a preparation containing an amount of at least one colonization factor which comprises culturing a host cell comprising a nucleotide sequence that encodes the colonization factor and a gene for resistance to an antibiotic in a growth medium having more than about 50 µg/ml of the antibiotic; centrifuging the growth medium; and filtering the growth medium. In preferred embodiments, the amount of the colonization factor obtained is about 1 milligram to about 20 milligrams per liter of growth medium used. The colonization factor may be a colonization factor antigen, a *coli* surface protein, or a putative colonization factor. In preferred embodiments, the colonization factor belongs to the CFA/I family, the CS5 family, the Type IV family, or the distinct group of colonization factors. In a more preferred embodiment, the colonization factor is CS6.

The host cell may be a bacterial cell such as an *Escherichia coli* cell. In preferred embodiments, the host cell is strain HB101. In preferred embodiments, the antibiotic is kanamycin. The growth medium may be a Luria broth, preferably, the growth medium is two times the concentration of Luria broth. In preferred embodiments, the growth medium contains about 100 µg/ml or more of the antibiotic. In some embodiments, the growth medium is filtered with a 0.2 µm filter tangential flow cartridge and a 300,000 MW cut-off filter. In some embodiments, the host cell is cultured at about 25° C. to about 37° C., preferably the host cell is cultured at about 30° C.

In some embodiments, the host cell is cultured until an absorbance reading of about 10 to about 21 at 600 nm. In some embodiments, a divalent cation such as calcium chloride may be added to the filter buffers. In some embodiments, the preparation made according to the present invention has a protein purity of the colonization factor of about 70% or more, preferably about 80% or more, more preferably about 90% or more, or even more preferably about 99% or more. In some embodiments, the preparation made according to the present invention comprises about 30 endotoxin units or less per mg of the colonization factor, preferably about 25 endotoxin units or less per mg of the colonization factor, more preferably about 20 endotoxin units or less per mg of the colonization factor, or even more preferably about 15 endotoxin units or less per mg of the colonization factor.

In some embodiments, the present invention provides a pharmaceutical composition comprising the preparation or the colonization factor made by the method of the present invention and a carrier, an adjuvant, or both. The pharmaceutical composition may be an oral formulation, an injectable formulation, an intranasal formulation, or a transcutaneous formulation. In preferred embodiments, the injectable formulation comprises about 10 to about 100 micrograms of the colonization factor and less than about 30 endotoxin units, preferably less than about 25 endotoxin units. In preferred embodiments, the pharmaceutical composition is an injectable formulation. In some embodiments, the pharmaceutical composition induces an immune response in a subject when administered to the subject. Preferably the subject is a mammal, more preferably the subject is a human. In preferred embodiments, the immune response induced in the subject is a mucosal immune response. In some embodiments, the pharmaceutical composition is formulated in one dose. In some embodiments, the dose comprises less than about 30 endotoxin units, preferably less than about 25 endotoxin units, more preferably less than about 20 endotoxin units.

In some embodiments, the present invention provides a method of preventing or inhibiting an enterotoxigenic *Escherichia coli* infection in a subject which comprises administering at least one preparation or at least one colonization factor made by the method of the present invention. Preferably the subject is a mammal, more preferably the subject is human. In preferred embodiments, the enterotoxigenic *Escherichia coli* infection is traveler's diarrhea. In some embodiments, the preparation or the colonization factor may be administered transcutaneously, intravenously, intranasally, or orally. In some embodiments, the preparation or the colonization factor induces an immune response in the subject when administered to the subject. In preferred embodiments, the immune response is a mucosal immune response.

In some embodiments, the present invention provides an oral pharmaceutical formulation comprising microencapsulated CS6 in a therapeutically effective amount.

In some embodiments, the present invention provides method of preventing or inhibiting an enterotoxigenic *Escherichia coli* infection in a subject which comprises administering an oral pharmaceutical formulation comprising microencapsulated CS6. In some embodiments, the present invention provides a method of immunizing a subject against an enterotoxigenic *Escherichia coli* infection which comprises administering to the subject an oral pharmaceutical formulation comprising microencapsulated CS6. In some embodiments, the method induces an immune response in the subject. Preferably the immune response is a mucosal immune response.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

Figure 1:
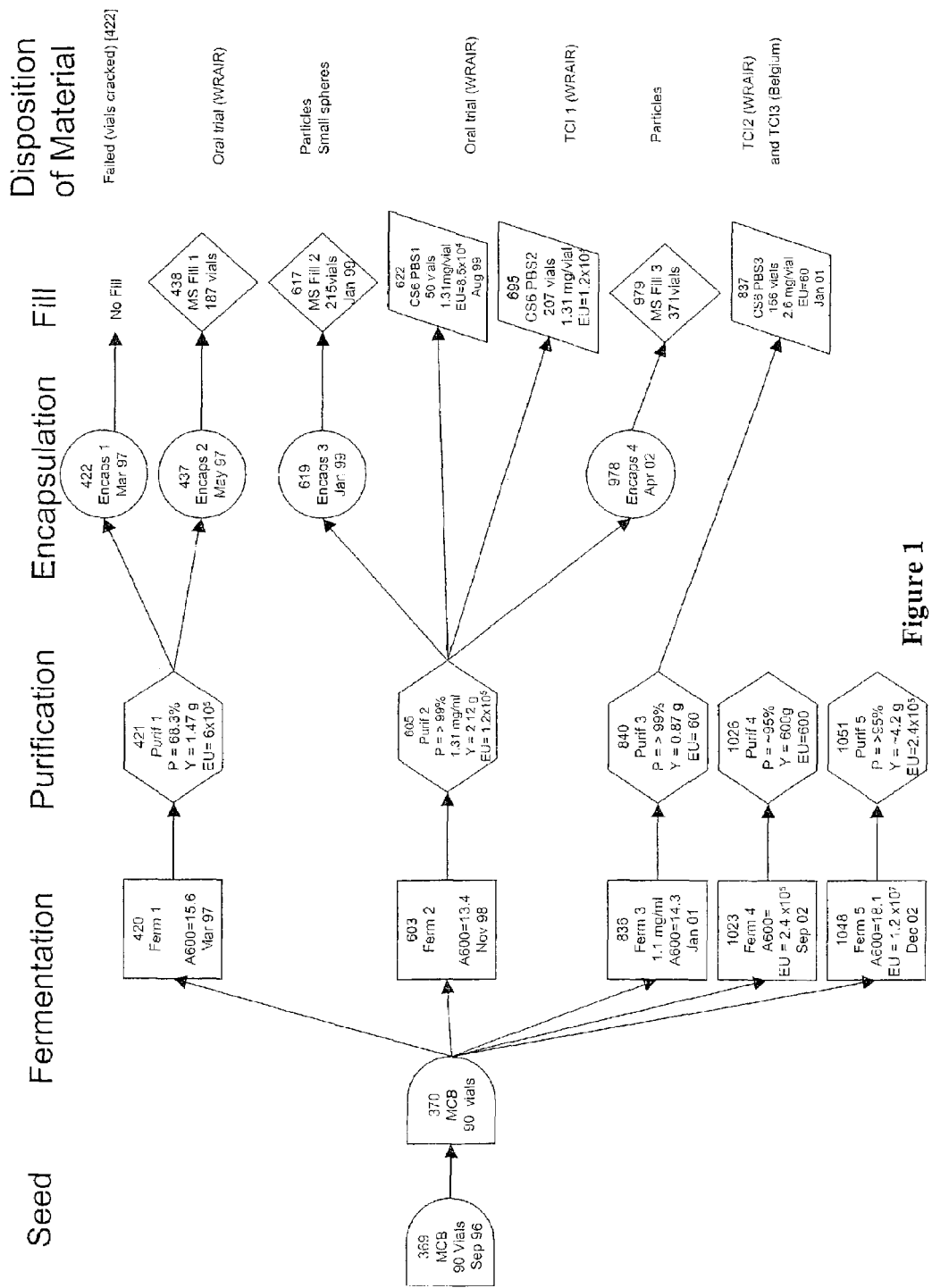
FIG. 1 is a schematic diagram of the process for making CS6.

The present invention generally provides a method of making at least one colonization factor (CF), such as CS6, in large amounts and high purity levels. In particular, the present invention provides a method of making at least one CF having a purity of greater than about 70%, preferably greater than about 80%, more preferably greater than about 90%, and even more preferably about 99% or more from about 10 liters or more, preferably about 100 L or more, and even more preferably about 300 L or more of initial bacterial culture. The CFs made by the method of the present invention may be incorporated into various pharmaceutical formulations and delivered to a subject via numerous routes. See e.g. International Application Publication No. WO 02/064162, and U.S. Pat. No. 6,309,669, which are herein incorporated by reference. As provided herein, the method of the present invention reduces chances for contamination during the production process and reduces the large number of assays required for quality control when small aliquots are pooled to make a final product.

Example 1 provides methods of making host cells comprising a DNA insert that encodes a CF of interest. Although the production of CS6 is exemplified herein, various CFs, including colonization factor antigens (CFAs), *coli* surface (CS) proteins, and putative colonization factors (PCFs), such as those provided in Table 1 may be made according to the present invention using conventional methods known in the art. See e.g. Wolf, M. K., et al. (1997) FEMS Microbiol. Letts. 148:35–42; see also U.S. Pat. No. 5,698,416, which are herein incorporated by reference.

TABLE 1

Morphologic and Size Characteristics of Colonization Factors of Human ETEC

| | | | | ULTRASTRUCTURE | |
|---|---|---|---|---|---|
| CF | CS | TOXINS | SUBUNIT MASS | TYPE* | DIAMETER (nm)** |
| I. CFA/I Family | | | | | |
| CFA/I | CFA/I | ST + LT, ST | 15,074 | rod | 7 |
| CS1 | CS1 | ST + LT | 15,233 | rod | 7 |
| CS2 | CS2 | ST + LT | 15,418 | rod | 7 |
| CS4 | CS4 | ST + LT | 14,961 | rod | 7 |
| PCFO166 | CS14 | ST | 15,029/15,541 | rod | 6–7 |
| CS17 | CS17 | LT | 15,375 | rod | 6–7 |
| CS19 | CS19 | ST + LT | 14,964 | rod | 7 |
| II. CS5 Family | | | | | |
| CS5 | CS5 | ST | 18,617 | flexible | 5–6 |
| CS7 | CS7 | ST + LT | 18,726 | helical | 3.5–6.5 |
| PCFO9 | CS13 | LT | 24,753 | flexible | unk |
| CS20 | CS20 | ST + LT | 17,524 | rod | 7 |
| PCFO20 | CS18 | ST + LT | 18,454 | rod | 7 |
| III. Type-IV Family | | | | | |
| CFA/III | CS8 | LT | 21,608 | rod | 7–8 |
| Longus | CS21 | ST + LT, ST, LT | 21,446 | rod | 7 |
| Arg-3 | CS22 | ST | 15,024 | flexible | n.d. |
| 8786 | CS15 | ST | 15,346 | AF | — |
| IV. Distinct | | | | | |
| CS3 | CS3 | ST + LT | 15,107/15,233 | curly | 2–3 |
| CS6 | CS6 | ST + LT, ST, LT | 15,058/15,877 | AF | — |
| PCFO148 | CS11 | ST + LT | unk | curly | 3 |
| PCFO159 | CS12 | ST + LT | 17,921 | rod | 7 |
| 2230 | CS10 | ST | 16,430 | AF | — |

*rod: rigid rod; AF: afimbrial (no known structure)
**unk: unknown; nd.: not determined Other peptides, polypeptides, and proteins in which an antibody raised against a native CF are cross-reactive to may also be made according to the present invention using conventional methods known in the art. See e.g. U.S. patent application Ser. No. 20010014668, which is herein incorporated by reference.

As described in Example 2, large amounts (greater than 3 L working volumes) of a given CF may be produced. Generally, an inoculum of host cells produced according to Example 1 was introduced into Luria broth media at 30° C. The culture is centrifuged and then filtered and then the CS6 protein was recovered and concentrated.

U.S. Pat. No. 5,698,416 ('416 patent) describes a small scale process for fermenting and isolating a CF, CS6, in low yields and purity levels of about 70% or less. The method of present invention comprises the following changes from the method disclosed in the '416 patent:

1. The host cells were cultured in media comprising more than 50 µg/l of antibiotic. In particular, the host cells were cultured in media comprising about 100 µg/l of antibiotic. It is noted that the standard amount of antibiotic is normally 50 µg/l and higher amounts of antibiotic is not usually recommended in the prior art. However, as described herein, using more than 50 µg/l of antibiotic increased the production of the given CF.

2. The host cells were harvested by first centrifuging the media and then filtering the supernatant. The method of the '416 patent harvested the host cells by filtering the media without any centrifugation. As described herein, total contamination was reduced by first centrifuging the media and then filtering.

3. Hollow fiber filter tangential flow cartridges filters of 0.2 µm and 300,000 MW cut-off filters were used rather than a flat plate Sarticon-Mini MF and UF filtration system (Sartorius, Edgewood, N.Y.). Hollow fiber systems allow more of the CF protein to remain intact (higher molecular weight) and therefore allow one to use a higher molecular weight cut off filter, i.e. 300,000 MWCO versus 100,000 MWCO with flat plate, and hence result in higher purity product.

4. Additionally, in the present method, a divalent cation was added to the filter buffers to reduce endotoxin.

As provided in Example 3, an oral vaccine comprising CS6 antigen microencapsulated in poly(DL-lactide-co-glycolide) (PLG) microspheres was tested. See Katz et al. (2003) Vaccine, 21(5–6):341–346; de Lormier, et al. (2003), Vaccine, 3754:1–8, in press; and see also Reid, R. H., et al. (1993) Vaccine 11:159–167 (CFA/II (containing CS3 and CS 1)), which are herein incorporated by reference. PLG is the same biodegradable material used in resorbable surgical sutures. The CS6 used in the test material was produced from genes cloned from ETEC strain E8775. See Wolf, M. K., et al. (1997) FEMS Microbiol Lett. 148(1):35–42, which is herein incorporated by reference. As provided in Example 3, the oral CS6 vaccine was safe and well tolerated in all 6 formulations. None of the vaccine-related symptoms met the definition of severe. All vaccine formulations elicited an immune response; there was at least one responder in each group. The observed immune response was similar in magnitude to experimental infection using a pathogenic strain of ETEC expressing CS6 and transcutaneous administration of CS6. See Güereña-Burgueño, F., et al. (2002) Infect. Immun. 70(4):1874–1880, which is herein incorporated by reference. Most peak responses were seen after the third dose of the vaccine, and support the use of three doses in subsequent studies.

Subjects of Group II, who received 1 mg of microencapsulated CS6 in buffer, did demonstrate the best immune response to the vaccine. Comparing the ASC response of Group II to its non-encapsulated counterpart (Group II) rendered a p=0.17. The microencapsulated formulation displayed the greatest reactogenicity of all of the groups. The microencapsulated CS6 in buffer formulation elicited the best mucosal and systemic immune response. Further experiments in mice show that the addition of an adjuvant to microencapsulated CS6 improves the immune response to CS6 (results unpublished). Thus, the present invention also provides compositions comprising microencapsulated CS6 and an adjuvant, such as LT, LT R192G, CT, and the like, and methods of treating diseases and disorders associated with ETEC comprising administering a therapeutically effective amount of CS6 and an adjuvant.

A CF made by the method of the present invention may be formulated into a variety of formulations suitable for administration. For example, a CF of the present invention may be formulated into a patch or biodegradable/biosorbable microspheres according to methods known in the art. In preferred embodiments, at least one CF such as CS6 may be incorporated into a trancutaneous patch or incorporated into a lactide-coglycolide biodegradable microsphere (PLGA) for oral administration. A CF made by the method of the present invention may be used as one component of a multivalent vaccine against ETEC infections. In preferred embodiments, the CF is CS6. Other suitable components of the multivalent vaccine include other colonization factors which include colonization factor antigens (CFAs), coli surface (CS) proteins, and putative colonization factors (PCFs), such as CS1–CS5, CFA/I–CFA/IV, and the like.

As used herein, "antibody" refers to immunoglobulin molecules and immunologically active portions that comprise an antigen binding site which specifically binds an antigen, such as a CF. Examples of immunologically active portions of immunoglobulin molecules include F(ab) and F(ab')$_2$ fragments which may be generated by treating the antibody with enzymes such as pepsin and papain. Polyclonal and monoclonal antibodies against the polypeptides of the present invention may be made by conventional methods known in the art. Antibodies of the present invention may be produced by conventional methods known in the art. See e.g., Coligan (1991) CURRENT PROTOCOLS IN IMMUNOLOGY. Wiley/Greene, N.Y.; and Harlow and Lane (1989) ANTIBODIES: A LABORATORY MANUAL, Cold Spring Harbor Press, N.Y.; Stites, et al. (1986) BASIC AND CLINICAL IMMUNOLOGY. 4th ed. Lange Medical Publications, Los Altos, Calif.; Goding (1986) MONOCLONAL ANTIBODIES: PRINCIPLES AND PRACTICE. 2d ed. Academic Press, New York, N.Y.; and Kohler and Milstein (1975) Nature 256:495–497, which are herein incorporated by reference. Therapeutic antibodies may be produced specifically for clinical use in humans by conventional methods known in the art. See Chadd, H. E. and S. M. Chamow (2001) Curr. Opin. Biotechnol. 12:188–194 and references therein, all of which are herein incorporated by reference.

The antigens or antibodies the present invention may be administered, preferably in the form of a pharmaceutical composition, to a subject. Preferably the subject is mammalian, more preferably, the subject is human. Preferred pharmaceutical compositions are those comprising at least one CF made by the method of the present invention or at least one antibody against a given CF, and a pharmaceutically acceptable vehicle. The immunogenic composition may be an active immunizing agent, such as a CF of the present invention, or a passive immunizing agent, such as an antibody raised against a given CF of the present invention. The immunogenic composition may elicit an immune response that need not be protective or the immunogenic composition may provide passive immunity. A vaccine elicits a local or systemic immune response that is protective against subsequent challenge by the immunizing agent such as a given CF. Accordingly, as used herein, an "immunogenic composition" can refer to vaccines as well as antibodies. A "protective immune response" may be complete or partial, i.e. a reduction in symptoms as compared with an unvaccinated mammal. As used herein, an "immunogenic amount" is an amount that is sufficient to elicit an immune response in a subject and depends on a variety of factors such as the immunogenicity of the antigen, the maimer of administration, the general state of health of the subject, and the like. The typical immunogenic amounts of a given CF such as CS6 for initial and boosting immunization for therapeutic or prophylactic administration ranges from about 0.001 mg to about 50 mg per about 65–70 kg body weight of a subject with a preferred range of 0.01 to 10 mg. For example, the typical immunogenic amount for initial and boosting immunization for therapeutic or prophylactic administration for a human subject ranges from about 0.05 mg to about 5 mg. Examples of suitable immunization protocols include initial immunization injections at time 0 and 4 or initial immunization injections at 0, 2, and 4 weeks, which initial immunization injections may be followed by further booster injections at ½ or 1 years.

As used herein, a "therapeutically effective amount" refers to an amount of an antigen that may be used to treat, prevent, or inhibit an infection caused by an organism expressing the antigen in a subject as compared to a control. Thus, a "therapeutically effective amount" may be an "immunogenic amount". For example, a "therapeutically effective amount" of CS6 refers to an amount of CS6 that may be used to treat, prevent, or inhibit an ETEC infection in a subject as compared to a control. Again, the skilled artisan will appreciate that certain factors may influence the dosage required to effectively treat a subject, including the severity of exposure to the organism, previous treatments, the general health and age of the subject, and the like. A therapeutically effective amount may be readily determined by conventional methods known in the art. It should be noted that treatment of a subject with a therapeutically effective amount of a CF of the present invention can include a single treatment or, preferably, can include a series of treatments.

The pharmaceutical compositions of the present invention may include an adjuvant. As used herein, an "adjuvant" refers to any substance which, when administered with or before the CF the present invention, aids the CF in its mechanism of action. Thus, an adjuvant in a vaccine is a substance that aids the immunogenic composition in eliciting an immune response. Suitable adjuvants include cholera toxin (CT), heat-labile toxin (LT), incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxy-phosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by conventional methods in the art.

The compositions of the present invention may be administered to a subject by any suitable route including oral, transdermal, intranasal, inhalation, intramuscular, and intravascular administration. It will be appreciated that the route of administration and pharmaceutical formulation will vary with the condition and age of the subject, the nature of the condition to be treated, the therapeutic effect desired, and the particular CF used. In preferred embodiments, the route of administration is oral, intranasal, parenteral, or transcutaneous.

As used herein, a "pharmaceutically acceptable vehicle" or "pharmaceutically acceptable carrier" refers to and includes any and all solvents, dispersion media, coatings, antibacterial and antifungal agents, isotonic and absorption delaying agents, and the like, that are compatible with pharmaceutical administration. Pharmaceutically acceptable vehicles include those known in the art. See e.g. REMINGTON: THE SCIENCE AND PRACTICE OF PHARMACY. 20$^{th}$ ed. (2000) Lippincott Williams & Wilkins. Baltimore, Md., which is herein incorporated by reference.

The pharmaceutical compositions of the present invention may be provided in dosage unit forms. "Dosage unit form" as used herein refers to physically discrete units suited as unitary dosages for the subject to be treated; each unit containing a predetermined quantity of the active agent calculated to produce the desired therapeutic effect in association with the required pharmaceutical carrier. The specification for the dosage unit forms of the invention are dictated by and directly dependent on the unique characteristics of the active agent and the particular therapeutic effect to be achieved, and the limitations inherent in the art of compounding such an active agent for the treatment of individuals.

The pharmaceutical formulations of the invention comprise at least one CF of the present invention and may be prepared in a unit-dosage form appropriate for the desired mode of administration. The pharmaceutical formulations of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen CF of the present invention.

It will be appreciated that the actual dosages of the CF used in the pharmaceutical formulations of this invention will vary according to the particular CF being used, the pharmaceutical formulation, the mode of administration, and the like. Optimal dosages for a given set of conditions may be ascertained by those skilled in the art using conventional dosage determination tests in view of the experimental data for a given CF.

Pharmaceutical formulations of this invention comprise a therapeutically effective amount of at least one CF of the present invention, and an inert, pharmaceutical or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art. Except insofar as any conventional media or agent is incompatible with a given CF, use thereof in the formulation is contemplated.

Supplementary active compounds can also be incorporated into the formulations. Supplementary active compounds include antimalarials, antibacterials, antiprotozoal agents, antifungal agents, and antidiarrheals and other compounds commonly used to treat bacterial, protozoal, and fungal infections, preferably ETEC infections. Supplementary active compounds include:

Antibiotics such as penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azitliromycin, clarithromycin, clindamycin, erythromycin, linecomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, ceplialothin, cefuroxime, ceftriaxone, vancomycin, gentamicin, amikacin, metronidazole, chloramphenicol, nitrofurantoin, co-trimoxazole, rifampicin, isoniazid, pyrazinamide, and the like;

Antiprotozoal agents such as chloroquine, doxycycline, mefloquine, metronidazole, eplomithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like;

Antifungal agents such as amphotericin B, fluconazole, itraconazole, ketoconazole, potassium iodide, flucytosine, and the like; and Antidiarrheal such as diphenoxylate, codeine phosphate, paregoric (camphorated opium tincture), loperamide hydrochloride, anticholinergics such as belladonna tincture, atropine, propantheline, kaolin, pectin, activated attapulgite, and the like.

A pharmaceutical formulation of the invention is formulated to be compatible with its intended route of administration. Examples of routes of administration include parenteral, e.g., intravenous, intradermal, subcutaneous, oral (e.g., ingestion), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of at least one CF is dissolved in an aqueous solution of an organic or inorganic acid, such as 0.3 M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0–60% of the total volume. The pharmaceutical formulation may also be in the form of a solution of a salt form of the active ingredient in an appropriate aqueous vehicle such as water or isotonic saline or dextrose solution.

The pharmaceutical formulations of the invention may be manufactured in manners generally known for preparing pharmaceutical compositions, e.g., using conventional techniques such as mixing, dissolving, granulating, drageemaking, levigating, emulsifying, encapsulating, entrapping or lyophilizing. Pharmaceutical formulations may be formulated in a conventional manner using one or more physiologically acceptable carriers, which may be selected from excipients and auxiliaries that facilitate processing of a given CF into preparations which can be used pharmaceutically.

Proper formulation is dependent upon the route of administration chosen. For injection, the CFs of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the CFs of the present invention can be formulated readily by combining with pharmaceutically acceptable carriers known in the art. Such carriers enable the CFs of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with at least one CF, optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum horoi, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Pharmaceutical formulations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the formulations may take the form of tablets or lozenges formulated in conventional manner.

Oral formulations generally include an inert diluent or an edible carrier. They can be enclosed in gelatin capsules or compressed into tablets. For the purpose of oral therapeutic administration, a given CF can be incorporated with excipients and used in the form of tablets, troches, or capsules. Oral formulations can also be prepared using a fluid carrier for use as a mouthwash, wherein the CF in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, a CF of the present invention may be conveniently delivered in the form of an aerosol spray presentation from syringe-based fine mist particle generators (e.g. Accuspray, Bectin-Dickinson), pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of at least one CF and a suitable powder base such as lactose or starch.

The CF of the present invention may be formulated for parenteral administration by injection, e.g., by bolus injection or continuous infusion.

Formulations for injection may be presented in unit-dosage form, e.g., in ampoules or in multi-dose containers, with an added preservative. The formulations may take such forms as suspensions, solutions or emulsions in oily or aqueous vehicles, and may comprise formulatory agents such as suspending, stabilizing and/or dispersing agents.

Pharmaceutical formulations suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the CF to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid horoidsene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the formulation. Prolonged absorption of the injectable compositions can be brought about by including in the formulation an agent which delays absorption, for example, aluminum monostearate and gelatin.

Sterile injectable solutions can be prepared by incorporating a therapeutically effective amount of at least one CF of the present invention in an appropriate solvent with one or a combination of ingredients enumerated above, as required, followed by filtered sterilization. Generally, dispersions are prepared by incorporating the CF of the present invention into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the CF plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the CF may be formulated into ointments, salves, gels, foams, powders, sprays, aerosols or creams as generally known in the art.

For example, for topical formulations, pharmaceutically acceptable excipients or cosmetically acceptable carriers and additives include solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art. Alternatively, CF of the present invention may be in powder form for constitution with a suitable vehicle, e.g., sterile pyrogen-free water, before use. The CF of the present invention may also be formulated in rectal compositions such as suppositories or retention enemas, e.g., comprising conventional suppository bases such as cocoa butter or other glycerides.

In addition to the formulations described above, CF of the present invention may also be formulated as a depot preparation. Such long-acting formulations may be administered by implantation (for example, subcutaneously or intramuscularly) or by intramuscular injection. Thus, for example, the CF of the present invention may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic CF is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic CFs well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical formulations may be employed. Liposomes and emulsions are known examples of delivery vehicles or carriers for hydrophobic drugs and cosmetics. Certain organic solvents such as dimethylsulfoxide also may be employed, although usually at the cost of greater toxicity. Additionally, the CF may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the CFs for a few weeks up to over 100 days. Depending on the chemical nature and the biological stability of the therapeutic reagent, additional strategies for protein stabilization may be employed.

The pharmaceutical formulations also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the CF of the invention may be provided as salts with pharmaceutically compatible counter ions. Pharmaceutically compatible salts may be formed with many acids, including hydrochloric, sulfuric, acetic, lactic, tartaric, malic, succinic, and the like. Salts tend to be more soluble in aqueous or other protonic solvents than are the corresponding free-base forms.

In one embodiment, a CF of the present invention is prepared with a carrier that will protect the CF against rapid elimination from the body, such as a controlled release formulation,; including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation, Boeringer-Ingelheim Corp., and Nova Pharmaceuticals, Inc. Liposomal suspensions can also be used as pharmaceutically or cosmetically acceptable carriers. These can be prepared according to methods known to those skilled in the art, for example, as described in U.S. Pat. Nos. 4,522,811 and 6,309,669, and International Application No. PCT/US91/03328, which are herein incorporated by reference.

Toxicity and therapeutic efficacy of the compositions of the present invention can be determined by standard pharmaceutical procedures in cell cultures or experimental animals. For example, one may determine the $LD_{50}$ (the dose lethal to 50% of the population), and the $ED_{50}$ (the dose therapeutically effective in 50% of the population) by conventional methods in the art. The dose ratio between toxic and therapeutic effects is the therapeutic index and it can be expressed as the ratio $LD_{50}/ED_{50}$. CFs which exhibit large therapeutic indices are preferred. While compounds or agents that exhibit toxic side effects may be used, care should be taken to design a delivery system that targets such compounds or agents to the site of affected tissue in order to minimize potential damage to uninfected cells and, thereby, reduce side effects.

The data obtained from the cell culture assays and animal studies can be used in formulating a range of dosage for use in humans. The dosage of the compositions of the present invention lies preferably within a range of circulating concentrations that include the $ED_{50}$ with little or no toxicity. The dosage may vary within this range depending upon the dosage form employed and the route of administration utilized. For any antigen used in the method of the invention, the therapeutically effective dose can be estimated initially from assays known in the art. A dose may be formulated in animal models to achieve a circulating plasma concentration range that includes the $IC_{50}$ (i.e., the concentration of the test compound which achieves a half-maximal inhibition of symptoms) as determined by conventional assays. Such information can be used to more accurately determine useful doses in humans. Levels in plasma may be measured, for example, by high performance liquid chromatography.

Immune responses to the CFs of the present invention may be determined using conventional methods known in the art. See e.g. Güereña-Burgueño, F., et al. (2002) Infect. Immun. 70(4):1874–1880; Reid, R. H., et al. (1993) Vaccine 11:159–167; Yu et al. (2002) Infect. Immun. 70(3):1056–1068; and Katz et al. (2003) Vaccine, 21(5–6): 341–346, which are herein incorporated by reference.

The following examples are intended to illustrate but not to limit the invention.

EXAMPLE 1

Construction of Host Cells Expressing CS6 Antigen

The host cells used for producing the CS6 batches disclosed in Example 2 were made according to the procedures described in U.S. patent Ser. No. 09/479,877, filed 10 Jan. 2000, which is herein incorporated by reference. See also Wolf, et al. (1997) FEMS Microbiology Letts. 148:35–42, which is herein incorporated by reference.

Generally, the genes for CS6 expression were from enterotoxigenic *Escherichia coli* (ETEC) strain E8775 tox⁻ of serotype 025:H42 which was a gift from Alejandro Cravioto. E8775 tox⁻is a derivative of *E. coli* stain E8775 which was origbally isolated from Bangladesh. DH5α which was purchased from Bethesda Research Laboratories, Inc. (Gaithersburg, Md.). pUC19 was originally purchased from P-L Biochem. The antibiotic resistance gene encodes resistance to kanamycin and was purchased from Pharmacia, Uppsala, Sweden (Kan® Genbiock®). However, other kanamycin resistance genes known in the art as well as genes for resistance to other antibiotics known in the art may be used. *E. coli* HB101 (ATCC 33694 and batch 91-1) was purchased from the American Type Culture collection (10801 University Blvd., Manassas, Va., 20110-2209).

The plasmid containing the CS6 genes, the pUC19 origin of replication, and the gene for kanamycin resistance was transformed into *E. coli* HB 101 by transformation using conventional methods known in the art. The transformants were selected by growth on L agar supplemented with 0.004% X-gal and 50 µg/ml kanamycin sulfate and optionally 50 µg/ml ampicillin. The plasmid comprising the CS6 gene was isolated from the strain and examined by agarose gel electrophoresis.

While the above protocol was used for obtaining a host cell that expresses CS6, other host cells, genes encoding other CFs, other antibiotic resistance genes, and conventional methods known in the art may be employed in accordance with the present invention.

EXAMPLE 2

Large Scale Production of CFs

Generally, an inoculum of host cells produced according to Example 1 was introduced into Luria broth media at 30° C. For simplicity, the temperature of the culture was maintained at about 30° C. during fermentation. However, the temperature of the culture may be increased to about 37° C. when growth is in the late mid-logarithmic phase ($A_{600}$ of greater than 6.0). The culture is centrifuged and then filtered and then the CS6 protein was recovered and concentrated. However, it is noted that where the desired CF protein is not in the supernatant, conventional methods known in the art may be used to obtain the CF protein from the bacterial cells and/or membranes. Further, other nutrient broths and media known in the art may be used in accordance with the present invention.

Figure 2:
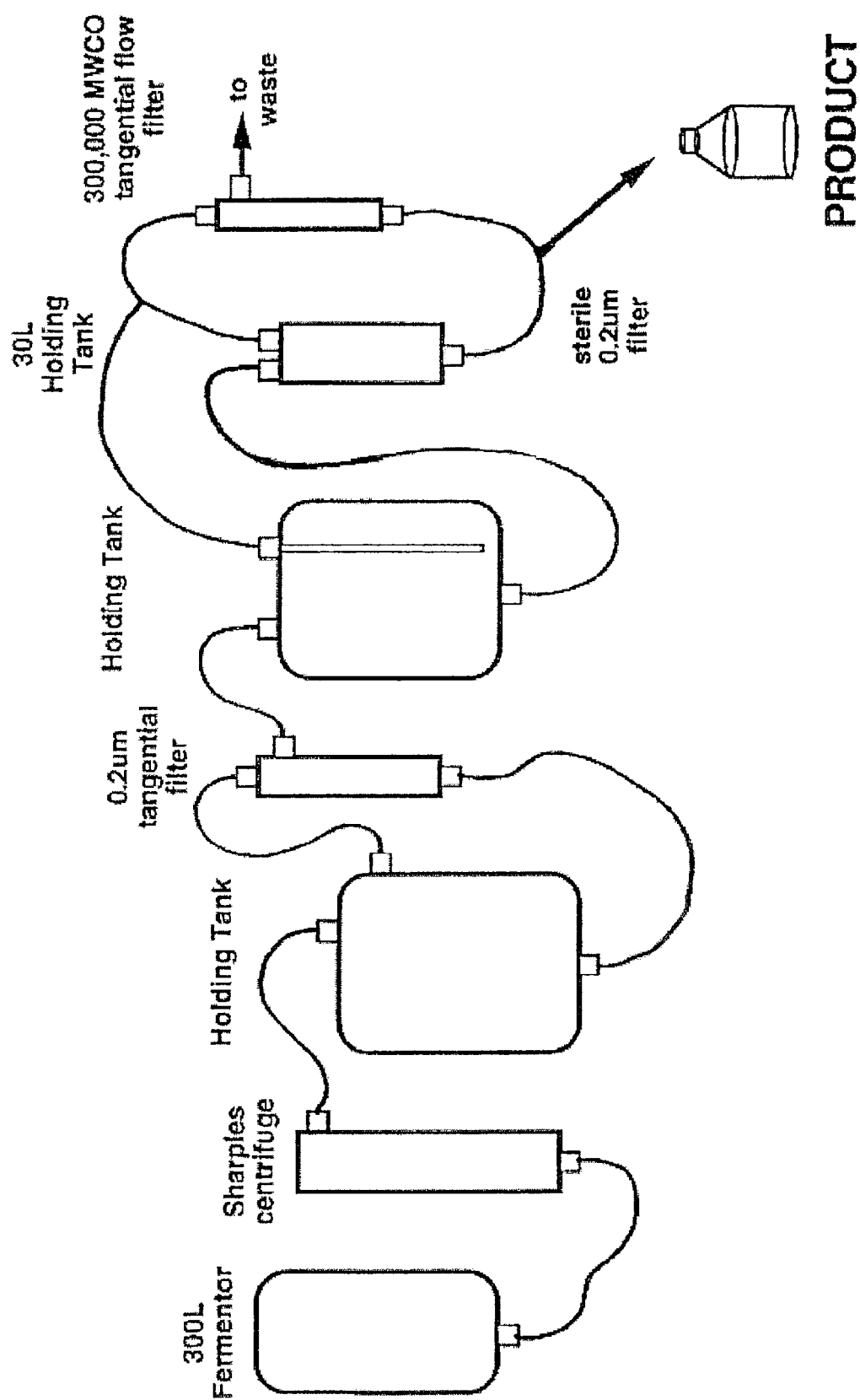
FIG. 2 is a schematic diagram of the fermentation and initial purification process.
Figure 3:
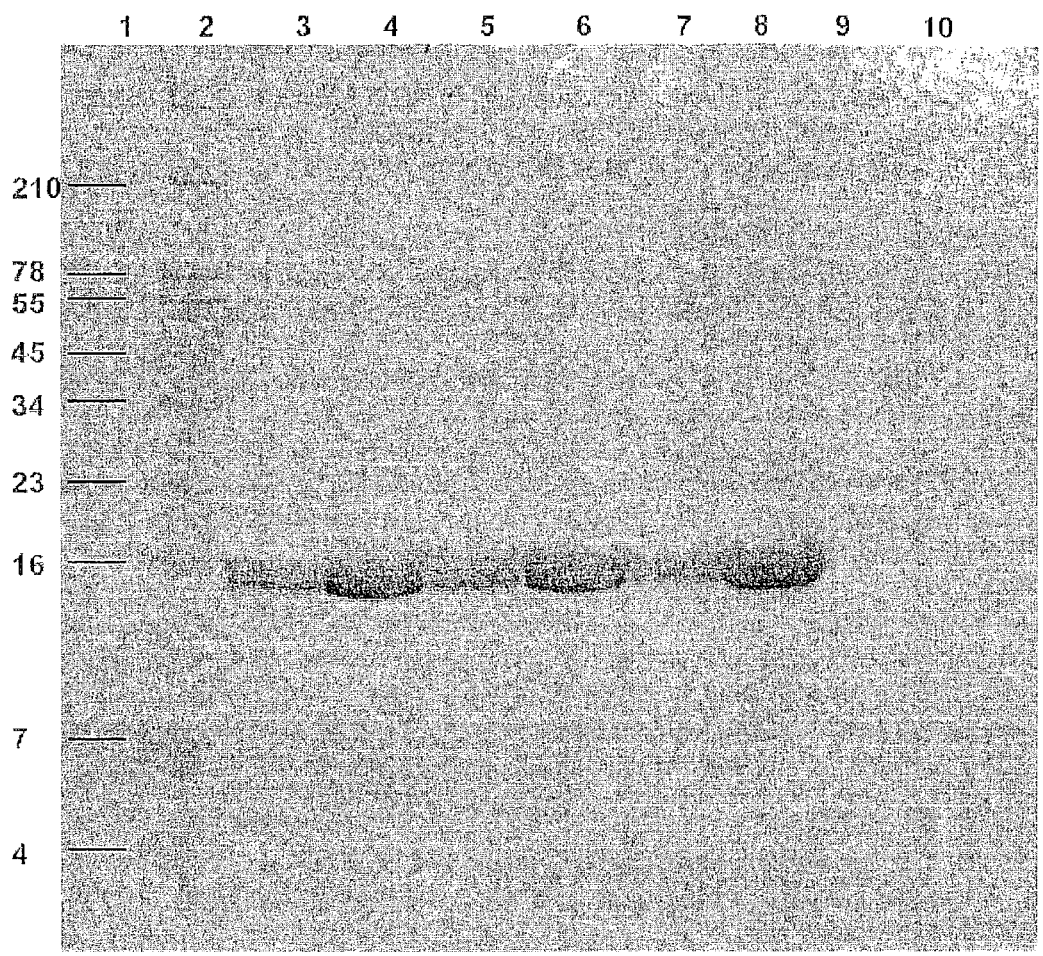
FIG. 3 is an SDS-PAGE of purified CS6 that shows a purity of greater than 99%.

Batches of CS6 antigen were produced according to good manufacturing procedures (GMP) according to the schematic set forth in FIG. 1. FIG. 2 is a schematic diagram of the fermentation and initial purification process. As provided in Table 2, the first batch yielded 1.4 grams of CS6, the second batch yielded 2.2 grams of CS6, the third batch yielded 1.0 gram of CS6.

TABLE 2

Summary of cloned strain M346 CS6 Fermentations at 10 L, 100 L, and 300 L cGMP L Levels

| Fermentation Date | Antibiotic | Harvest $OD_{600}$ | Harvest Wet weight (g) | Broth CS6 (mg) | Protein Purity |
|---|---|---|---|---|---|
| 10 L | | | | | |
| | Km 100 | 15.9 | 239 | 122 | 94% |
| | Km 200 | 17.3 | 242 | 144 | 89% |
| | Km 200 | 20.9 | 247 | 43 | 93% |
| | Km 100 | 15.6 | 215 | 102 | 93% |
| 100 L | | | | | |
| | Km 100 | 13.0 | 1990 | 3550 | 99% |
| | Km 200 | 10.7 | 1980 | 1010 | 90% |
| 300 L cGMP | | | | | |
| | Km 50 | 15.6 | ND | 1400 | 68% |
| | Km 100 | 12.9 | 5800 | 2200 | 99% |
| | Km 200 | 14.3 | 6040 | 1000 | 99% |

Km = kanamycin concentration in µg/ml

Protein purity was determined by SDS-PAGE. See FIG. 4. As provided in Table 2, the protein purity of the CS6 batches made ranged from about 68% to about 99%. It is important to note that when 50 µg/ml of antibiotic was used, the protein purity obtained was only about 68%. Therefore, in preferred embodiments of the present invention, more than about 50 µg/ml of antibiotic are used, more preferably about 100 µg/ml of antibiotic are used.

The amounts of endotoxin were also measured by the *Limultis* amebocyte lysate (LAL) Pyrotell assay (Associates of Cape Cod Inc., Falmouth, Mass.) for the detection and quantification of bacterial endotoxin by the gel-clot method known in the art. However, other conventional methods known in the art may be used. The 300 L cGMP batches comprised $6.0 \times 10^5$, $8.5 \times 10^4$, and 60 EU per ml of sample, respectively, or $2.9 \times 10^5$, $6.4 \times 10^4$, and 23 EU per mg of protein, respectively. Therefore, the present invention provides CF preparations having less than about 30 EU/mg protein, preferably less than about 25 EU/mg protein, more preferably less than about 20 EU/mg protein, and even more preferably less than about 15 EU/mg protein. As the antigenic dose of CS6 is about 1.0 mg of protein, the present invention also provides less than about 30 EU/dose of CS6, more preferably less than about 25 EU/dose of CS6, and more preferably less than about 20 EU/dose of CS6.

For production of CS6 from a 10 L working volume, a Bioflow III fermentor (New Brunswick Scientific, Edison, N.J.) with a 14 liter glass vessel (10 liter working volume) was used. The media used was prepared using Luria broth media at 2× concentration with 0.4% glycerol and comprised 200 g tryptone (Difco Laboratories, Detroit, Mich.), 100 g yeast extract (Difco Laboratories, Detroit, Mich.), 200 g NaCl, and 40 ml glycerol. The L broth (2×) contained twice the concentration of the original recipe by Luria. The broth was adjusted to provide a total volume of 10 liters. The media was then autoclaved. After the media had cooled to about 45° C., kanamycin was added to provide a concentration of 100 µg/ml. A 100 ml mid-log phase inoculum (1/100 inoculum volume) of about $3.2 \times 10^9$ cells/ml of bacterial cells comprising a DNA insert encoding a CS6 antigen was added.

The CS6 antigen was purified by first centrifuging the media and then filtering the supernatant (about 80% of the CS6 is in the supernatant, the remaining CS6 resides on the cells, therefore, additional extraction and purification of the pellet is not necessary) using a 0.2 µm filter tangential flow cartridge (CFP-2-E6A, 2800 $cm^2$; Pharmacia/AG Technologies Corp., Needham, Mass.) and then passing the filtrate through a 300,000 MW cut-off filter (UFP-500-C6A, 4800 $cm^2$; Pharmacia/AG Technologies Corp., Needham, Mass.), which retains the CS6 protein. Filtration followed manufacturer's instructions and specifications.

Calcium and other divalent cations crosslink to endotoxin molecules to form a complex that may be filtered or purified away from a desired CF. Therefore, calcium chloride was added to the filter buffers. Alternatively, other divalent cations known in the art may be used. The initial harvest supernatant was diluted 1:1 in phosphate buffered saline (PBS) with 0.5 mM $CaCl_2$, then all wash buffers contained PBS with 0.25 mM $CaCl_2$.

For production of CS6 from a 300 L working volume, a New Brunswick Scientific 400 L Fermentor System (New Brunswick Scientific, Edison, N.J.) with a 400 L stainless steel steam-in-place vessel (300 liter working volume) was used. The media used was prepared using Luria broth media at 2× concentration with 0.4% glycerol and comprised 6,000 g tryptone (Difco Laboratories, Detroit, Mich.), 3000 g yeast extract (Difco Laboratories, Detroit, Mich.), 6000 g NaCl, and 1200 ml glycerol. The L broth (2×) contained twice the concentration of the original recipe by Luria. The broth was adjusted to provide a total volume of 300 liters. The media was then autoclaved. After the media had cooled to about 45° C., kanamycin was added to provide a concentration of 100 µg/ml. A 3 L mid-log phase inoculum (1/100 inoculum volume) of about $3.2 \times 10^9$ cells/ml of bacterial cells comprising a DNA insert encoding a CS6 antigen was added.

The CS6 antigen was purified by first centrifuging the media and then filtering the supernatant (about 80% of the CS6 is in the supernatant, the remaining CS6 resides on the cells, therefore, additional extraction and purification of the pellet is not necessary) using a 0.2 µm filter tangential flow cartridge (Pharmacia/AG Technologies Corp., Needham, Mass.) and then passing the filtrate through a 300,000 MW cut-off filter, which retains the CS6 protein. Calcium chloride was added to the filter buffers.

As only a limited quantity of calcium can be added to phosphate containing buffers due to calcium phosphate precipitation, other divalent cations and non-phosphate buffers known in the art may be used such that higher concentrations of divalent cations may be used to remove more endotoxin amounts. For example, Tris based buffers (e.g. Tris (10 mM), NaCl (150 mM), $CaCl_2$ (20 mM), pH 7.6) that will allow much higher concentrations of divalent cations may be used in accordance with the present invention.

Figure 4:
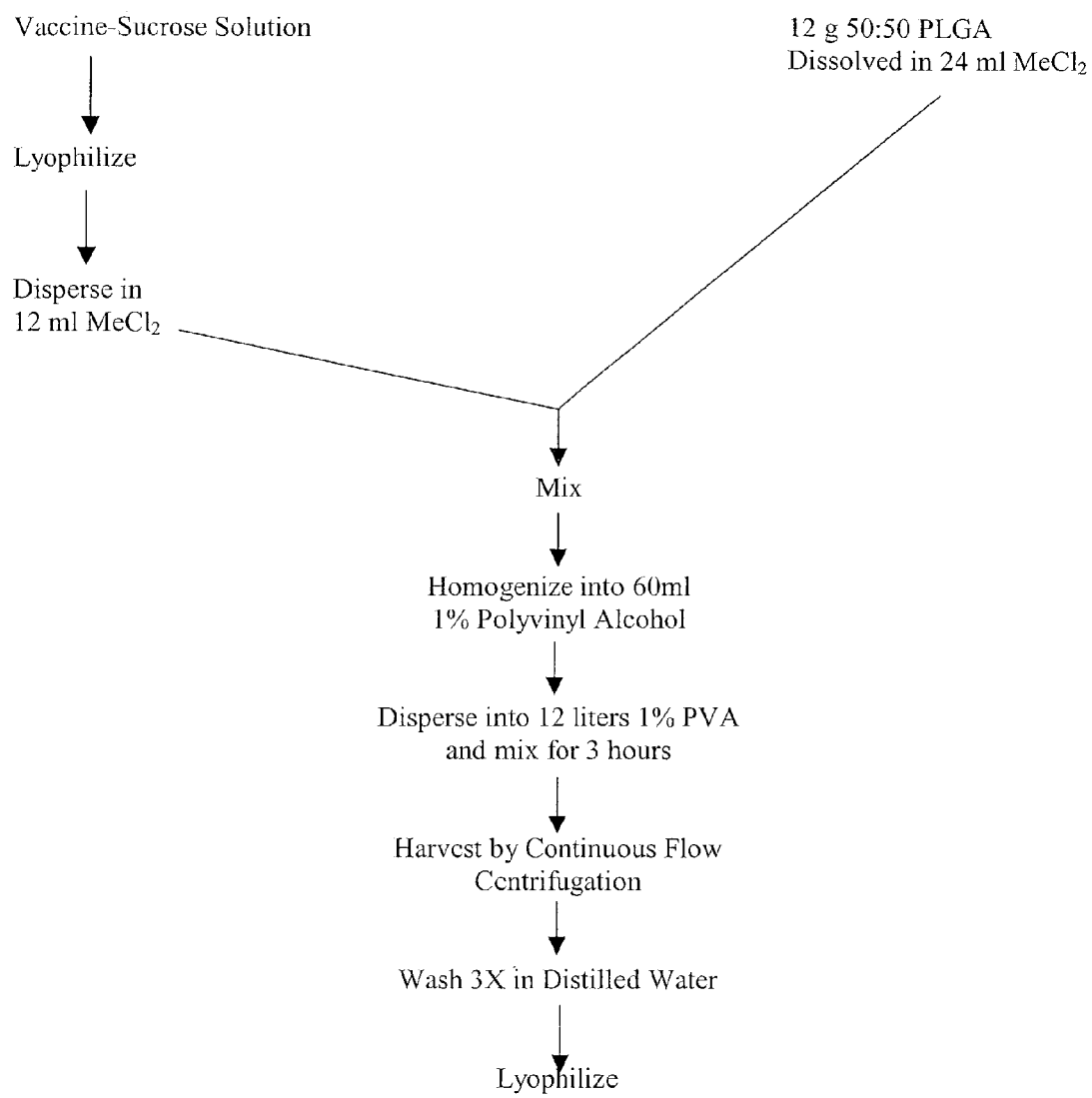
FIG. 4 is a schematic diagram of the antigen in aqueous sucrose solution being incorporated into PLGA by a solvent evaporation procedure.

Then sucrose was added and the antigen in aqueous sucrose solution was lyophilized and then incorporated into PLGA by a solvent evaporation procedure as shown in FIG. 4. See also U.S. Pat. No. 6,309,669, and International Application PCT/US91/03328, which are herein incorporated by reference. The antigen/sucrose mixture was dispersed into a polymer-methylene chloride solution which was then homogenized into a polyvinyl alcohol solution (PVA). After evaporation of the methylene chloride from the mixture, the resulting microspheres were harvested by centrifugation.

The pelleted microspheres were resuspended in water, aliquoted (2 ml) into serum vials (20 ml) and lyophilized.

The resulting product was examined by scanning electron microscopy, biochemical analysis, microbial load assays, and safety and immunogenicity tests. See Katz et al., (2001) Vaccines for Enteric Diseases Abstracts, 7–9; Katz et al. (2003) Vaccine, 21(5–6):341–346; and de Lorimier et al. (2003) Vaccine, 3754:1–8, in press, which are herein incorporated by reference.

Vaccine preparations comprising a CF, such as CS6, have been tested in subjects. See e.g. Yu et al. (2002) Infect. Immun. 70(3): 1056–1068 (transcutaneous mice); Güereña-Burgueño, F., et al. (2002) Infect. Immunity 70(4):1874–1880 (transcutaneous human); de Lorimier, et al. (2003) Vaccine, 3754:1–8, in press, (intranasally mice); and Katz et al. (2003) Vaccine, 21(5–6):341–346 (oral microencapsulated human); and Bryd and Cassels (2003) Vaccine, 3688:1–10, in press, (intranasally and intragastrically mice); which are herein incorporated by reference.

EXAMPLE 3

Oral Formulation Comprising Microencapsulated CS6

A. Clinical Study 1

The safety and immunogenicity of CS6, a multi-subunit protein commonly found on the surface of ETEC, was evaluated according to the following experiments.

Generally, the formulations tested included 1 and 5 mg doses of CS6, either encapsulated in biodegradable polymer poly (D,L)-lactide-co-glycolide, or as free protein, administered orally in a solution of either normal saline or a rice-based buffer. Three doses of CS6 were given at 2 week intervals. Blood was collected immediately before and 7 days after each dose. All formulations were well tolerated. Four of five subjects who received 1mg CS6 in PLG microspheres with buffer had significant IgA ASC responses (median=30 ASC per $10^6$ PBMC) and significant serum IgG responses (median=3.5 fold increase). Oral administration of this prototype ETEC vaccine is safe and can elicit an immune response. The ASC, serum IgA, and serum IgG responses to CS6 are similar in magnitude to the responses after challenge with wild type ETEC (Coster et al., unpublished).

Healthy male and female subjects, age 18–45, were recruited from the Washington, DC, metropolitan area. All subjects were assigned a code to maintain confidentiality. Subjects were excluded from participation in the study if they met any of the following criteria: travel to a developing country within 1 year of study participation and experienced diarrhea, received a cholera vaccination within 5 years of the study, participated in previous enteric vaccine protocols, had a clinically significant illness, history of chronic gastrointestinal illness, positive pregnancy test, was unable or unwilling to submit blood samples, use of stomach acid neutralizer within 2 days of the study, had occupational exposure to ETEC or Vibrio cholerae, or participated in another vaccine challenge study within 30 days of this protocol.

Six (6) formulations of the vaccine as shown in Table 3 were tested.

TABLE 3

| Group | Form | Buffer | Dose | Number |
| --- | --- | --- | --- | --- |
| I | Non-encap | Yes | 1 mg CS6 | 4 |
| II | PLG | Yes | 1 mg CS6 | 5 |
| III | PLG | No | 1 mg CS6 | 3 |
| IV | Non-encap | Yo | 5 mg CS6 | 4 |
| V | PLG | Yes | 5 mg CS6 | 5 |
| VI | PLG | No | 5 mg CS6 | 5 |

CS6 and CS6 microencapsulated in PLG microspheres (CS6-PLG) were produced under current good manufacturing practices (cGMP) at the WRAIR Pilot Bioproduction Facility, Silver Spring, Md. The bacterial strain used for the production of CS6 was constructed from E. coli (HB101) containing a recombinant plasmid carrying the four genes necessary for CS6 expression. See Wolf, M. K., et al. (1997) FEMS Microbiol Lett. 148(1):35–42, which is herein incorporated by reference. The major components in the production included: bacterial fermentation, recovery of the CS6 from the fermentation broth by tangential flow filtration, ammonium sulfate precipitation, buffer exchange from PBS into 4% sucrose, microencapsulation by a solvent evaporation procedure using an emulsion of CS6/sucrose and PLG in methylene chloride, homogenization in polyvinal alcohol, removal of methylene chloride by evaporation, lyophilization, and storage at −80° C. Unencapsulated CS6 was produced in an identical manner to the microencapsulated CS6, but the material was stored in PBS at −80° C.

The vaccine was administered orally in three doses. There were 6 vaccine groups (Table 3). Groups I–III (low dose; 1 mg each dose) were vaccinated on days 0, 14, and 28. Groups IV–VI received their three doses (high dose; 5 mg, 4 mg, and 4 mg, respectively) on days 7, 21, and 35. On the day of vaccination, all subjects were observed 90 minutes prior to and after vaccine administration. The subjects drank from a cup which contained either CS6 or CS6-PLG in 100 ml of either normal saline or buffer (Cera Products LLC, Jessup, Md.). Subjects then drank from a second cup containing 50 ml of either normal saline or buffer (to match the solution in the first cup).

Subjects kept a diary to record any symptoms that occurred for the seven days following each dose. The diary collected solicited and unsolicited symptoms and intensities. Symptom presence and intensity was graded: not present; mild (noticeable, but did not interfere with routine activities); moderate (interfered with routine activities); or severe (unable to perform routine activities). Fever was defined as a temperature greater than 100.5° F. and documented by Temp-dot (3M, Rochester, Minn.) disposable thermometers. The number of vomiting episodes were recorded as were the number of episodes diarrhea (defined as about 3 or more loose stools over a 24 hour period), and loose stools. The subjects returned on the day after vaccination and seven days post-vaccination for clinical assessment and to monitor for any possible side-effects. The diaries were reviewed by the study physicians with the subjects.

CS6-specific antibody-secreting cell (ASC) immune responses to the vaccine antigen were chosen as a surrogate of intestinal mucosal immune response. See Wenneras, C., el al. (1992) Infect Immun. 60:2605–11, which is herein incorporated by reference. Whole blood was collected for ASC's weekly from the day of the first vaccination (prior to receiving the vaccine) until 2 weeks after the third vaccination (a total of 7 samples). Blood specimens were collected using EDTA treated tubes (Becton Dickinson Vacutainer Systems, Rutherford, N.J.). Peripheral blood mononuclear cells (PBMC) were isolated from the blood sample by gradient centrifugation on Ficoll-Hypaque (Sigma Co., St. Louis, Mo.) and were assayed for total and CS6-specific numbers of IgA ASC by the ELISpot technique. See Wenneras, C., et al. (1992) Infect Immun. 60:2605–11 and Czerkinsky, C., et al. (1998) J. Immunol. Methods 115:31–37, which are herein incorporated by reference. Individual wells of nitrocellulose-bottom 96-well plates (Millititer HA; Millopore Corp., Bedford, Mass.) were coated with 0.1 ml of purified CS6 (20 µg/ml) as the solid phase antigen, and incubated overnight at 4° C. After being washed with PBS, the plates were blocked with complete Iscove's medium (GibcoBRL, Grand Island, N.Y.) supplemented with 5% fetal calf serum (GibcoBRL) and 50 µg/ml gentamycin (GibcoBRL). The PBMC were adjusted to $2 \times 10^7$ viable cells/ml in complete Iscove's medium. A final 0.1 ml suspension containing $10^6$ PBMC was added to each well, and plates were incubated for 4 hours at 37° C. in 7.5% $CO_2$. Plates were washed, incubated overnight at 4° C. with goat anti-human IgA horseradish peroxidase (IgA) (Southern Biotech Associates, Birmingham, Ala.), and exposed to chromogen-enzyme substrate (Sigma, St. Louis, Mo.). Spots, corresponding to a zone of antibodies secreted by individual cells, were enumerated in triplicate wells under 40× magnification, with data expressed as the number of spot-forming cells per $10^6$ PBMC.

A positive ASC response was defined as about a 2-fold or more increase over baseline value of the ASC's per $10^6$ PBMC, when the number of ACS's was about 0.5 per $10^6$ PBMC or more in the baseline sample. If the number of pre-immune ASC's was less than 0.5 per $10^6$ PBMC, a value of greater than about 1.0 per $10^6$ PBMC after dosing was considered a positive response. Serum was collected weekly simultaneously with whole blood (for the ASC assay). IgA and IgG antibody titers against the CS6 antigen were determined by ELISA. See Hall, E. R., et al. (2001) Infect. Immun. 69(5):2853–7, and Jertborn, M., et al. (1998) Vaccine 16:255–260, which are herein incorporated by reference. Individual microtiter wells (Nuncimmunoplates, Roskilde, Denmark) were coated with 0.1 ml of a 1.0 µg/ml preparation of CS6 at 37° C. overnight. The plates were washed with PBS and then blocked with 0.1% bovine serum albumin (Sigma, St. Louis, Mo.). Serum samples were diluted 1:5 then 3 fold serially and incubated at room temperature for 90 minutes. Bound antibodies were visualized by addition of rabbit anti-human IgA or IgG conjugated with horseradish peroxidase (Jackson ImmunoResearch Laboratories, Westgrove, Pa.) and incubated at room temperature for 90 minutes followed by addition of o-phenylenediamine (OPD)-$H_2O_2$ (Sigma, St. Louis, Mo.). The endpoint titers were assigned as the interpolated dilutions of the samples giving an absorbance value at 450 nm of 0.4 above background. Titers were adjusted in relation to a reference specimen included in each test to compensate for day-to-day variation. Pre- and post-dosing serum samples from the same individual were tested side by side. The antibody titer ascribed to each sample represented the geometric mean of duplicate determinations performed on different days. Reciprocal endpoint titers less than 5 were assigned a value of 2.5 for computations. Based on calculations of the methodological error of each ELISA, a response was defined as about a two-fold increase or more in endpoint titer between pre- and post-immunization, with the added criterion that the post-immunization reciprocal titer be about 10 or more. Seroconversion after any dose was defined as a positive response.

The Fishers exact test was used to compare proportions. Graphs were constructed to contrast each group (formulation). There were no significant differences in the frequency or the magnitude of the serum antibody or ASC response to CS6 between the 6 groups. Therefore, data were pooled for further presentation.

The ages of the 29 subjects who participated in this study ranged from 20 to 44 years of age. Nineteen of the subjects were African American, six were Caucasian, one was Hispanic, and three were of other nationalities/ethnicities. Among the 29 subjects who received a study agent, three subjects received one dose, three subjects received two doses, and 23 received all three doses. Only one subject withdrew because the subject was unable to drink the vaccine (1 mg CS6 in buffer) due to the taste of the buffer. Five subjects did not receive the full three doses. Specifically, two did not receive the full three doses due to scheduling conflicts, two did not receive the full three doses due to lack of follow-up, and one did not receive the full three doses due to illness. Only the 26 subjects that received 2 or more doses of the vaccine were included in the safety and immune data analysis.

In general, the vaccine was well tolerated. Half of the subjects (13 of 26) reported minor symptoms that were possibly vaccine-related, such as abdominal gurgling (31%), headache (27%), abdominal cramps (19%), nausea (19%), diarrhea (12%), and malaise (12%). Twelve of 26 subjects reported mild symptoms, five reported moderate symptoms of abdominal cramps, abdominal gurgling, headache or malaise. None reported severe symptoms. Group II (1 mg CS6-PLG in buffer) had the greatest proportion of subjects reporting symptoms. See Table 4.

TABLE 4

The Number of Subjects Reporting Symptoms Possibly Related to the Vaccine

| Group | Number | Mild | Moderate | Severe |
|-------|--------|------|----------|--------|
| I | 4 | 2 | 0 | 0 |
| II | 5 | 4 | 1 | 0 |
| III | 3 | 2 | 1 | 0 |
| IV | 4 | 1 | 0 | 0 |
| V | 5 | 2 | 2 | 0 |
| VI | 5 | 2 | 1 | 0 |

Over half of the subjects reported symptoms judged not to be vaccine-related based on clinical context. One subject met the definition of diarrhea about 2 to about 3 days after the third dose. This was linked to ingestion of copious amounts of Mylanta. Two subjects experienced two loose stools, one 2 days after the second dose and one within 24 hours of the third dose. Three subjects experienced one loose stool, one 5 days after the third dose, one 2 weeks after the third dose, and one 8.5 hours and 6 days after the third dose.

Figure 5:
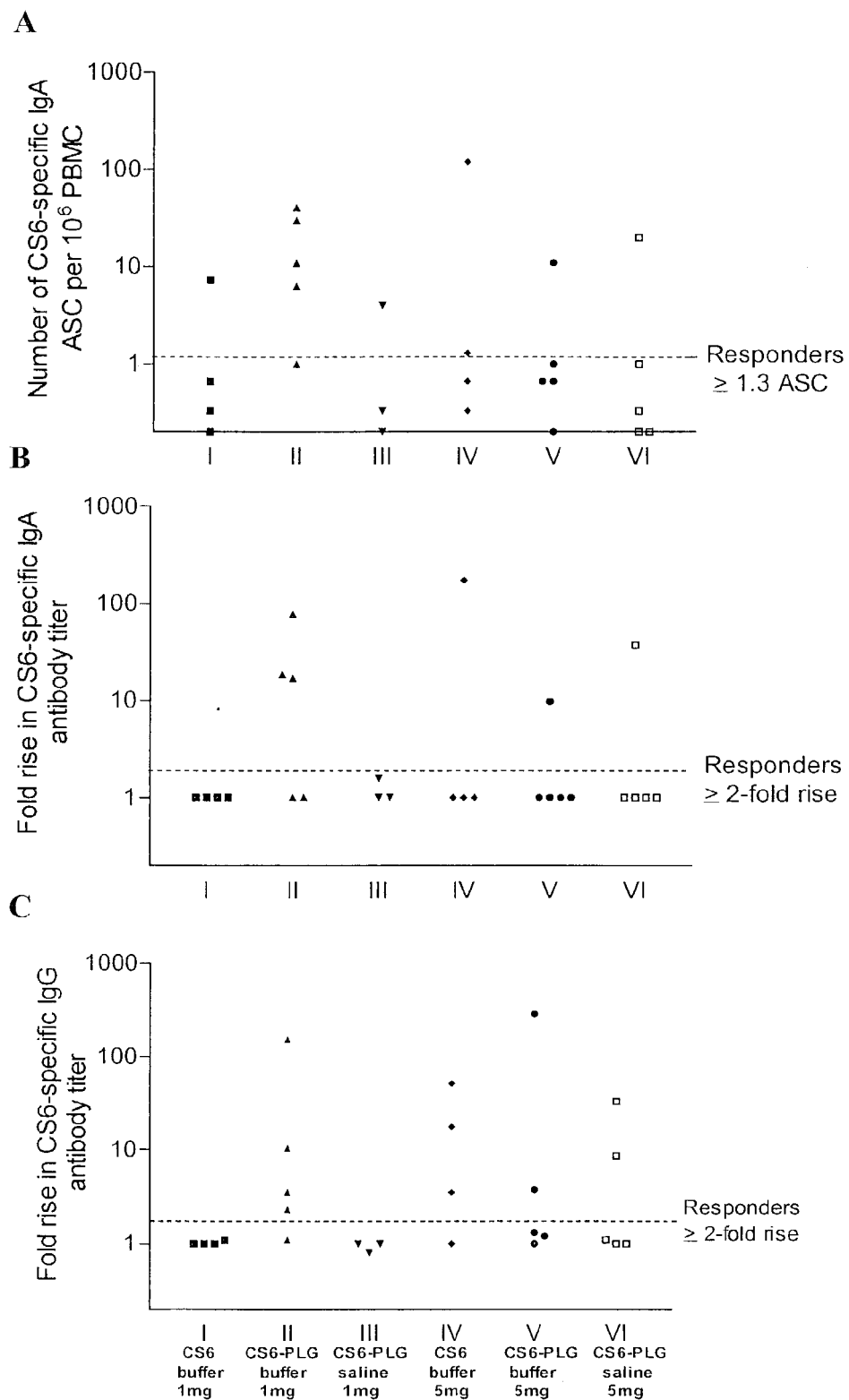
FIG. 5A shows the frequency and magnitude of anti-CS6 IgA ASC (antibody secreting cells) responses to CS6.
FIG. 5B shows the peak fold increase in serum IgA antibody titers to CS6.
FIG. 5C shows the peak fold increase in serum IgG antibody titers to CS6.

The frequency and magnitude of anti-CS6 IgA ASC responses are shown in FIG. 5A. Ten of 26 (40%) subjects showed an ASC response to CS6 (ranging from 1.33–120). There was no apparent difference for ASC response to microencapsulated (7 of 18) and unencapsulated (3 of 8) CS6. There was a better response at the low dose when looking at encapsulated forms regardless of the buffer being used. There were more ASC responses in the groups with buffer (8 of 18) than with normal saline (2 of 8). The best responses were seen in Group II. Applying Fishers exact test to Group 11 and its non-encapsulated counter part (Group I) rendered a p=0.17. Of the responders in Group II (4 of 5), one subject had a peak ASC response after the first dose, one after the second dose, and two after the third dose.

Six of 26 (24%) subjects showed a serum IgA response to CS6 (ranging from 9.8–174 fold increase). Peak fold increase in serum IgA titers can be seen in FIG. 5B. Serum IgA responses to microencapsulated CS6 (5 of 18) was greater than the response to unencapsulated CS6 (1 of 8), and responses to vaccines given with buffer (5 of 18) were greater than responses given in normal saline (1 of 8).

Eleven of 26 (44%) subjects showed a serum IgG response to CS6 under the criteria of a 2-fold increase (ranging from 2.3–288). Peak fold increase in serum IgG titers can be seen in FIG. 5C. There was no apparent difference for serum IgG response to microencapsulated (8 of 18) and unencapsulated (3 of 8) CS6. There were more IgG responses in the groups with buffer (9 of 18) than with normal saline (2 of 8).

B. Clinical Study 2

As provided herein an oral vaccine against ETEC was studied. The formulations tested included CS6 encapsulation in microspheres in 1 mg and 5 mg doses, and a rice-based buffer. The microspheres are biodegradable and permit slow and continued release of antigen for increased exposure to the immune system. The microspheres were made of biodegradable polymer poly(D,L-lactide-co-glycolide) (PLG). The test vaccine was produced using Good Manufacturing Practices (GMP) at the Walter Reed Army Institute of Research Bioproduction Facility in Silver Spring, Md. Three doses of CS6 in PLG microspheres were given in normal saline (NS) or CeraVacx (CV) a rice-based bicarbonate solution to neutralize stomach acid. Human subjects were divided into groups and administered the formulations according to Table 5.

TABLE 5

| Group | Form | Buffer | Dose 1 | Doses 2 and, 3 | N |
| --- | --- | --- | --- | --- | --- |
| I | — | CV | 1 mg CS6 | 1 mg CS6 | 4 |
| II | PLG | CV | 1 mg CS6 | 1 mg CS6 | 5 |
| III | PLG | NS | 1 mg CS6 | 1 mg CS6 | 3 |
| IV | — | CV | 5 mg CS6 | 4 mg CS6 | 4 |
| V | PLG | CV | 5 mg CS6 | 4 mg CS6 | 5 |
| VI | PLG | NS | 5 mg CS6 | 4 mg CS6 | 5 |

Subjects fasted for 90 minutes, swallowed 100 ml of CV or NS containing CS6, swallowed another 50 ml of CV or NS containing CS6, and fasted an additional 90 minutes. The subjects received additional doses two and four weeks later. Subjects were interviewed and provided with diary sheets to record symptoms for the five days following each vaccination. Whole blood was collected from the subjects weekly for 7 weeks to measure immune responses to CS6. CS6-specific IgA production by antibody-secreting cells (ASC) was measured as a surrogate of mucosal immune response, and CS6-specific immunoglobulins IgA and IgG levels in sera were determined.

All formulations were well tolerated; none of the subjects reported symptoms definitely related to the vaccines, while half of the subjects reported possible vaccine-related symptoms. The most common symptoms were abdominal gurgling (10), headache (7) abdominal cramps (5), nausea (5), loose stools (5), and malaise (2). Five subjects reported moderate symptoms that interfered with some aspect of their daily routines: two reported abdominal cramps, two reported abdominal gurgling, one reported a headache, and one reported malaise. The subjects were not clustered around any dose or associated with any group.

No subject reported diarrhea that was judged to be vaccine-related. Five reported one or two loose stools that were possibly vaccine related. Three of the subjects reported loose stools after the third dose, one after the first dose, and one after the second. The subjects were not clustered in any group.

Table 6 summarizes the number of subjects reporting symptoms possibly related to the vaccination.

TABLE 6

| Group | Diarrhea | Loose Stools | Mild | Moderate | Severe |
| --- | --- | --- | --- | --- | --- |
| I | 0 | 1 | 2 | 0 | 0 |
| II | 0 | 1 | 4 | 1 | 0 |
| III | 0 | 1 | 2 | 1 | 0 |
| IV | 0 | 0 | 1 | 0 | 0 |
| V | 0 | 1 | 2 | 2 | 0 |
| VI | 0 | 1 | 2 | 1 | 0 |

Immunogenicity and immune responses tested by conventional methods known in the art. Table 7 summarizes the frequency of the immune responses to CS6.

TABLE 7

| Group | N | ASC | Serum IgA | Serum IgG | /Any |
| --- | --- | --- | --- | --- | --- |
| I | 4 | 1 | 0 | 0 | 1 |
| II | 5 | 4 | 3 | 4 | 4 |
| III | 3 | 1 | 0 | 0 | 1 |
| IV | 4 | 2 | 1 | 3 | 3 |
| V | 5 | 1 | 1 | 2 | 2 |
| VI | 5 | 1 | 1 | 2 | 2 |
| Any | 26 | 10 | 6 | 11 | 13 |

Only Group II (1 mg CS6 in PLG microcapsules delivered in CV) had median peak responses to CS6 above the baseline for all three immune parameters. Group IV (5 mg CS6 delivered in CV) had a median peak serum IgG response above the baseline. The median responses of all other groups were not above the baseline.

Most of the subjects that had ASC or serum IgG responses to CS6 responded before the third dose while their first serum IgA response was after the third dose. Most subjects had peak responses to CS6 after the 3rd dose of vaccine.

The frequency and magnitude of immune responses to CS6 was similar to those measured after challenge of subjects with ETEC strain B7A, that expresses CS6 (Coster et al., unpublished).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of making a purified preparation of an amount of at least one *Escherichia coli* colonization factor comprising culturing an *E. coli* host cell that comprises a nucleotide sequence encoding the colonization factor and a gene for resistance to an antibiotic in a growth medium having about 100 µg/ml or more of the antibiotic; centrifuging the growth medium; and filtering the growth medium with a hollow fiber tangential flow cartridge filter of 0.2 μm and a filter having 300,000 MW cut-off using a filter buffer containing a divalent cation to obtain said purified preparation, wherein the purified preparation comprises about 30 endotoxin units or less per mg of the colonization factor.

2. The method of claim 1, wherein the amount is about 1 milligram to about 20 milligrams per liter of the growth medium.

3. The method of claim 1, wherein the colonization factor is a colonization factor antigen, a coli surface protein, or a putative colonization factor.

4. The method of claim 1, wherein the colonization factor belongs to the CFA/I family, the CS5 family, the Type IV family, or the distinct group of colonization factors.

5. The method of claim 1, wherein the *E. coli* host cell is *E. coli* HB101.

6. The method of claim 1, wherein the antibiotic is kanamycin.

7. The method of claim 1, wherein the growth medium is Luria broth.

8. The method of the claim 7, wherein the gLuria broth is 2× Luria broth.

9. The method of claim 1, wherein the growth medium contains about 200 μg/ml or more of the antibiotic.

10. The method of claim 1, wherein the *E. coli* host cell is cultured at about 25° C. to about 37° C.

11. The method of claim 10, wherein the *E. coli* host cell is cultured at about 30° C.

12. The method of claim 1, wherein the *E. coli* host cell is cultured until an absorbance reading of about 10 to about 21 is reached at 600 nm.

13. The method of claim 1, wherein the divalent cation is calcium chloride.

14. The method of claim 1, wherein the colonization factor has a purity of about 70% or more.

15. The method of claim 14, wherein the colonization factor has a purity of about 80% or more.

16. The method of claim 15, wherein the colonization factor has a purity of about 90% or more.

17. The method of claim 16, wherein the colonization factor has a purity of about 99% or more.

18. The method of claim 1, wherein the purified preparation comprises about 25 endotoxin units or less per mg of the colonization factor.

19. The method of claim 18, wherein the purified preparation comprises about 20 endotoxin units or less per mg of the colonization factor.

20. The method of claim 19, wherein the purified preparation comprises about 15 endotoxin units or less per mg of the colonization factor.

21. A method of making a purified preparation of an amount of *coli* surface antigen 6 (CS6) of *Escherichia coli* comprising culturing *E. coli* host cell HB101 that comprises a nucleotide sequence encoding the CS6 and a gene for resistance to kanamycin in a growth medium having about μg/ml or more of kanamycin; centrifuging the growth medium; and filtering the growth medium with a hollow fiber tangential flow cartridge filter of 0.2 μm and a filter having 300,000 MW cut-off using a filter buffer containing a divalent cation to obtain said purified preparation, wherein the purified preparation comprises about 30 endotoxin units or less per mg of the CS6.

* * * * *